United States Patent
Lee et al.

(10) Patent No.: US 6,339,719 B1
(45) Date of Patent: Jan. 15, 2002

(54) APPARATUS AND METHOD FOR DETECTING SOUNDS FROM A HUMAN BODY AND DISPLAYING THE DETECTED SOUND INFORMATION

(75) Inventors: Myun Woo Lee, Seoul; Chang Kyu Cho, Kyunggi-do; Cha Ryong Koo, Kyunggido; Jung Ki Kim, Seoul, all of (KR)

(73) Assignee: Hitouch Inc. (KR)

( * ) Notice: Subject to any disclaimer, the term of this patent is extended or adjusted under 35 U.S.C. 154(b) by 0 days.

(21) Appl. No.: 09/600,161
(22) PCT Filed: Feb. 1, 1999
(86) PCT No.: PCT/KR99/00049
   § 371 Date: Aug. 1, 2000
   § 102(e) Date: Aug. 1, 2000
(87) PCT Pub. No.: WO99/38431
   PCT Pub. Date: Aug. 5, 1999

(30) Foreign Application Priority Data
   Feb. 2, 1998 (KR) .............................................. 98-2839

(51) Int. Cl.[7] ................................................. A61B 5/02
(52) U.S. Cl. ...................................... 600/511; 600/528
(58) Field of Search ................................. 600/511, 514, 600/528, 300; 381/67

(56) References Cited

U.S. PATENT DOCUMENTS

| | | | | |
|---|---|---|---|---|
| 5,301,679 A | * | 4/1994 | Taylor ......................... | 600/511 |
| 5,524,631 A | * | 6/1996 | Zahorian et al. ............. | 600/586 |
| 5,730,140 A | * | 3/1998 | Fitch ........................... | 600/514 |
| 6,126,595 A | * | 10/2000 | Amano et al. ............... | 600/300 |

\* cited by examiner

Primary Examiner—George R. Evanisko
(74) Attorney, Agent, or Firm—Arent Fox Kintner Plotkin & Kahn, PLLC

(57) ABSTRACT

The present invention provides an apparatus and method for detecting sounds from a human body and displaying the detected sound information. The apparatus comprises a stethoscope for collecting sounds, a piezoelectric device for converting the collected sounds into an electric signal, a speaker for converting the electric signal into audible sound, an A/D converter for digitizing the electric signal, a memory for storing the digitized sound data, a microprocessor for issuing the switch control signal, extracting features of the stored data, analyzing the extracted feature values statistically, storing the analyzed statistical figures in the memory, and reading out the statistical figures from the memory, and an LCD panel for displaying the LCD signals.

5 Claims, 2 Drawing Sheets

APPARATUS AND METHOD FOR DETECTING SOUNDS FROM A HUMAN BODY AND DISPLAYING THE DETECTED SOUND INFORMATION

TECHNICAL FIELD

The present invention relates generally to an apparatus and method for detecting sounds from a human body and displaying the detected sound information, and more particularly, but not by way of limitation, to a portable apparatus which enables to not only collect minute sounds from a human body, such as the heartbeat of an unborn baby or the pulsation of an ordinary person and amplify the collected sounds over a speaker, but also display feature values of the collected sounds such as the number of heartbeats and the amplitude of the beat sounds in relation to reference feature values, and to the method employed therein.

BACKGROUND ART

In daily lives, people often want or need to listen to some minute sounds from their bodies. For example, a pregnant woman may desire to listen to her unborn baby's heartbeat and ascertain if her baby is in good condition. Some people may want to check their pulsation while doing exercise.

Such tasks, however, are not easy to do and sometimes require time and cost. To check an unborn baby's heartbeat, the mother should go to hospital with special instruments designed exclusively for the object, which results in the loss of time and money. To count the number of beats as a measure for maintaining the amount of exercise constant, one should feel one's artery at the wrist and count the number of beats during an interval and calculate the number of beats per minute using the counted number, which might be troublesome.

DISCLOSURE OF INVENTION

The present invention has been developed to solve the foregoing problems. It is a primary object of the present invention is to provide an apparatus and method for detecting sounds from a human body and displaying the collected sound information, the apparatus being portable and easily used to collect minute sounds from a human body and amplifies the collected sounds over a speaker.

The apparatus for detecting sounds from a human body and displaying the detected sound information according to the present invention comprises sound collecting means for collecting arbitrary sounds, extracting means for extracting feature values from the collected sounds, storing means for storing the extracted feature values, comparing means for comparing the extracted feature values with representative values of previously extracted feature values, displaying means for visually displaying the relation between the extracted feature values and the representative values, and updating means for updating the representative values to include the last extracted feature values.

The method for detecting sounds from a human body and displaying the detected sound information according to the present invention comprise the steps of 1) intermittently collecting sounds from a human body, 2) extracting feature values of the intermittently collected sounds, 3) updating previously calculated representative values to include the extracted feature values, and 4) displaying the updated feature values and extracted feature values.

Used usually as a portable device like a wrist watch, the apparatus according to the present invention collects intermittent sounds by properly positioning the sound collecting means when needed, extracts feature values of the collected sounds using the extracting means, and stores the extracted feature values in the storing means.

Next, the apparatus compares the extracted feature values and representative values of previously obtained and stored feature values using the comparing means and displays the comparison result in a visually appealing manner using graphs. The representative values are updated to include the newly extracted feature values so that the updated representative values can be used in the next measurement.

The apparatus for detecting sounds from a human body and displaying the detected sound information according to the present invention enables visual display of feature values of collected sounds in relation to the average of the previously obtained feature values as well as simply collecting minute sounds from a human body and amplifying the collected sounds over a speaker.

The invention may be embodied in other specific forms without departing from the sprit or essential features thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

BRIEF DESCRIPTION OF DRAWINGS

The accompanying drawings, which are included to provide a further understanding of the invention, illustrate a preferred embodiment of this invention, and together with the description serve to explain the principles of the present invention.

In the drawings.

MODES FOR CARRYING OUT THE INVENTION

The preferred embodiment of the present invention will be described in detail referring to the accompanying drawings.

Figure 1:
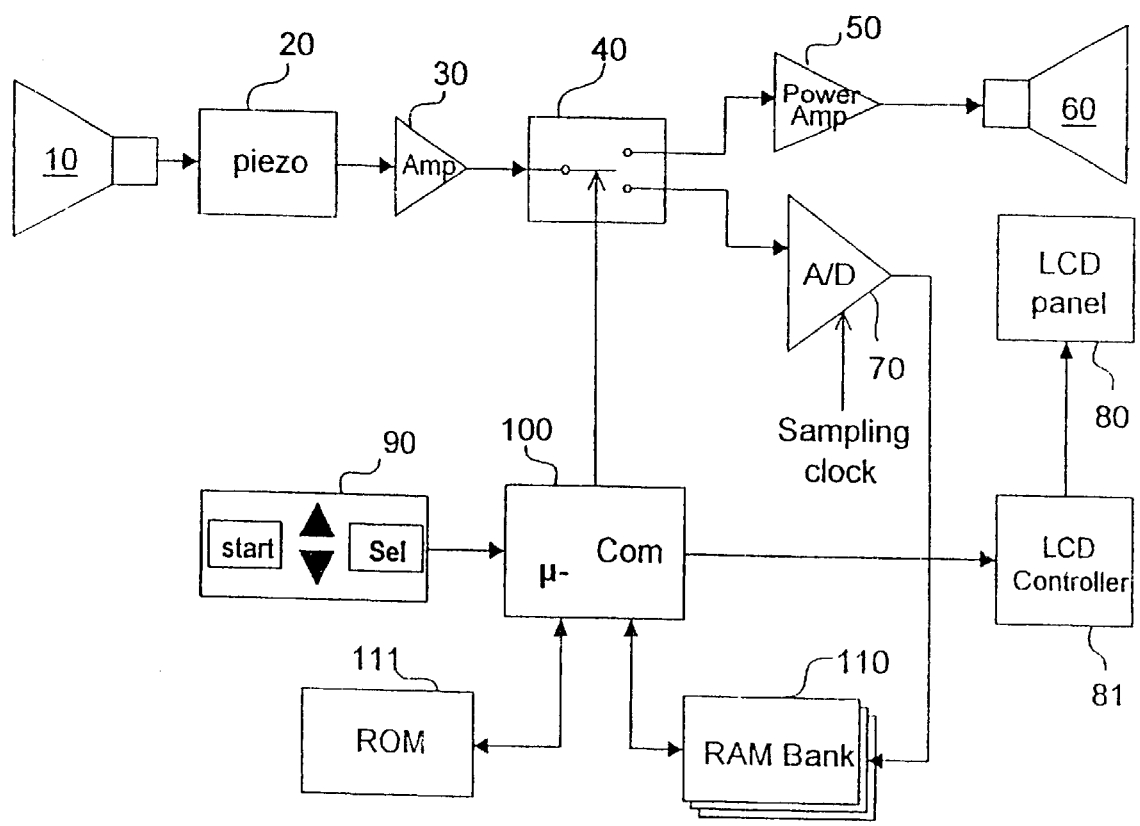
FIG. 1 is a schematic diagram of an apparatus for detecting sounds from a human body and displaying the sound information as an embodiment of the present invention.
Figure 2:
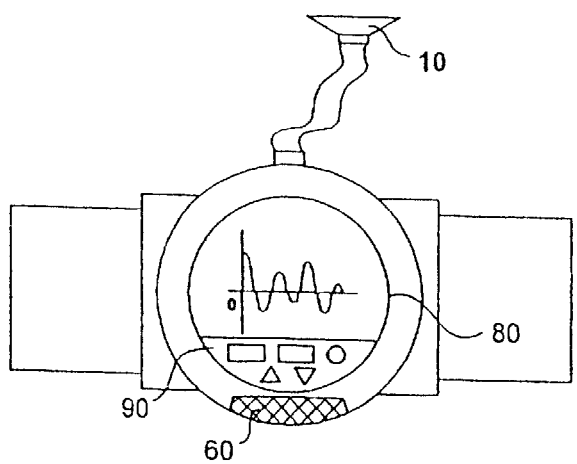
FIG. 2 is an schematic diagram of an apparatus for detecting sounds from a human body and displaying the sound information applied to a wrist watch as an embodiment of the present invention.

FIG. 1 illustrates an apparatus for detecting sounds from a human body and displaying the detected sound information as an embodiment of the present invention. FIG. 2 shows the apparatus in FIG. 1 applied to a wrist watch, comprising a stethoscope 10 for collecting sounds from a particular position of a human body, a piezoelectric device 20 for converting the collected sounds into an electric signal, an amplifier 30 for amplifying the electric signal, a switch 40 for connecting the amplified electric signal to one of the output according to a control signal, a power amplifier 50 for amplifying the power of the electric signal received from the switch 40, a speaker 60 for converting the power-amplified electric signal into an audible sound, an A/D converter 70 for digitizing the electric signal outputted from the switch 40, a memory 110 for storing the digitized sound data, an input device 90 for receiving users' instructions, a microprocessor 100 for issuing the aforementioned control signal, executing a program stored in a ROM 111 to extract features of the data stored in the memory 110, performing statistical analysis of the extracted feature values, storing the analyzed statistical figures in the memory 110, and reading out the statistical figures from the memory 110, an LCD control unit 81 for converting the data read by the microprocessor 100 into LCD display signals, and an LCD panel 80 for displaying the converted LCD display signals.

Considering the fact that the apparatus in FIG. 2 is applied to a wrist watch, it is desirable that the stethoscope 20 should be freely removable when unnecessary. In addition, the stethoscope 20 employed as a sound collecting device can be replaced with a Doppler ultrasonic probe or other sound collecting devices.

Figure 3:
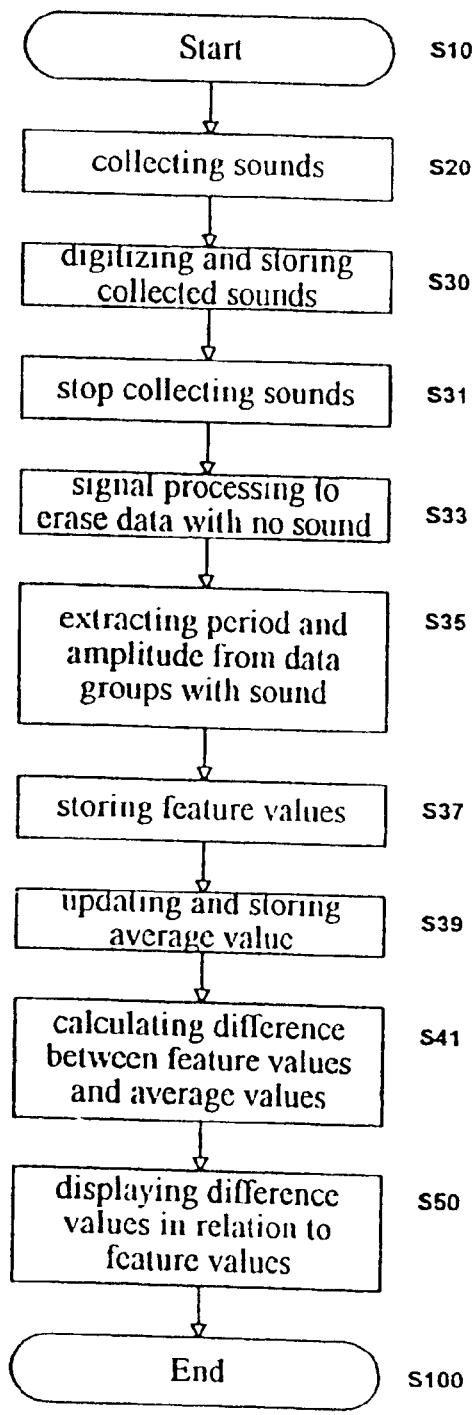
FIG. 3 is a flowchart of the method for detecting sounds from a human body and displaying the detected sound information according to the present invention.

FIG. 3 is a flow chart of the method for detecting sounds from a human body and displaying the detected sound information according to the present invention. The operation of the apparatus in FIG. 2 is explained below in detail with reference to the flow chart.

When necessary, a user attaches the removable stethoscope 10 to a wrist watch with the apparatus according to the present invention installed and enters basic information and conditions required for measurement to be performed using the input device 90. The wrist watch can be usually used as an ordinary watch.

The basic information and conditions to be entered include: the object (the heartbeat of an infant or unborn baby or the pulsation of a normal person), the preferred presentation method of the measurement result (audible sound by simple amplification of the detected sounds or visual display of the result of various analyses of the detected sounds), and numbers for comparing the feature values of the detected sounds with reference feature values. After the necessary information and conditions are entered, the stethoscope is properly positioned and the sound collecting operation begins (S20). The position of the stethoscope 10 can be the left breast of an infant, or the stomach of a pregnant woman, depending upon the object.

The sounds collected by the stethoscope 10 are converted into an electric signal by the piezoelectric device 20, amplified by the amplifier 30, and then applied to the switch 40. The amplitude of the converted electric signal is proportional to the volume of the collected sounds.

In response to the user's instruction received by the input unit 90, the microprocessor 100 issues a control signal to the switch 40 for determining the output port of the switch 40. If the user simply requests to listen to the detected sounds using a speaker, the electric signal applied to the switch 40 is connected to the power amplifier 50. In contrast, if the user wants to obtain visually displayed information including the result of the comparison between the features of the detected sounds such as the period of heartbeat and reference feature values, the amplified electric signal applied to the switch 40 is connected to the AID converter 70.

In the former case, the amplified electric signal outputted from the switch 40 is applied to the speaker 60 after power amplification by the power amplifier 50. The speaker converts the electric signal into audible sound, so that the user can hear the heartbeat of an infant or pulsation. In the latter case, the amplified electric signal outputted from the switch 40 is digitized by the A/D converter 70 with a sampling rate of about 10 Hz and the digitized data are stored in the memory 110 (S30).

Controlling the switch 40 after collecting sounds during a given interval, the microprocessor 100 stops the sound collecting operation (S31). And then, executing the program stored in the ROM 111, the microprocessor 100 performs digital signal processing such as deletion of digital data corresponding to intervals with no sound information in order to minimize the required amount of the memory 110 (S33).

Using the information on the sampling rate, the number of deleted digital data with no sound information, and the like, the microprocessor 100 extracts feature values such as the period of the groups of digital data with sound information and their amplitudes (S35). The extracted feature values are stored in the memory 110 (S37).

The microprocessor 100 updates the average of each feature value using the currently extracted feature values and feature values previously obtained and stored in the memory 110 (S39), and finds the differences between the currently obtained feature values and the previous feature values (S41). The difference and average values are transferred to the LCD control unit 81 which yields LCD display signals so that the feature values can be displayed on the LCD panel 80 in a visually appealing manner using graphs (S50). Step 539 for updating the average of each feature value can be conducted after displaying the data, on the LCD panel 80.

In the above process, it is possible to use other representative values such as the most frequently measured value as well as average. It is also feasible to visually present the distribution of feature values such as variance and standard deviation using graphs so that each feature value can be easily perceived with reference to the distribution.

As a modified embodiment of the present invention, the wrist watch may have the stethoscope 10 installed in the backside. This apparatus does not necessitate placing the stethoscope 10 at a particular position, since it can count the number of beats using the internally installed stethoscope. A user has only to set the measurement mode to see the counting result while doing exercise like jogging It is also feasible to embody the present invention without the switch 40 so that the amplification of the sounds over a speaker can be conducted currently with displaying the feature values and their statistical information on the LCD panel.

The present invention has been described with reference to a specific embodiment of the wrist watch-form. The present invention, however, can be embodied in any form of portable devices such as a waist belt, table clock.

What is claimed is:

1. An apparatus for detecting sounds from a human body and displaying the detected sound information, comprising:

a means for collecting arbitrary sounds;

a means for amplifying and outputting sound of the collected sounds;

a means for extracting feature values from the collected sounds;

a means for allowing user selection and for switching the collected sounds from the collecting means to the sound outputting means or the feature extracting means based on the user's selection;

a means for storing representative values of previously extracted feature values and the extracted feature values;

a means for comparing the extracted features values with the representative values of previously extracted feature values;

a means for displaying a relation between the extracted feature values and the representative values to include the last extracted feature values; and a means for updating the representative values to include the last extracted feature values.

2. An apparatus according to claim 1, wherein said arbitrary sounds include the sound of heartbeat of an unborn baby.

3. An apparatus according to claim 1, wherein said feature values include the period of occurrence of sounds.

4. An apparatus according to claim 1, wherein said feature value include the amplitude of sounds.

5. An apparatus according to claim 1, wherein said displaying means displays said extracted feature values in the form of graphs with respect to the representative value.

* * * * *